US006720153B1

(12) United States Patent
Labaudiniere et al.

(10) Patent No.: US 6,720,153 B1
(45) Date of Patent: Apr. 13, 2004

(54) LUCIFERASE REPORTER BIOASSAY OF PARATHYROID HORMONE COMPOUNDS

(75) Inventors: Richard F. Labaudiniere, Collegeville, PA (US); Kin T. Yu, Limerick, PA (US); Gregg R. Crumley, Philadelphia, PA (US); Clarence C. Morse, Royersford, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/387,176

(22) Filed: Aug. 31, 1999

Related U.S. Application Data
(60) Provisional application No. 60/099,188, filed on Sep. 4, 1998.

(51) Int. Cl.$^7$ .................. G01N 33/53; C12N 15/00; C12N 5/00; C12N 5/08
(52) U.S. Cl. .................. 435/7.1; 435/320.1; 435/325; 435/7.21; 435/8; 435/366
(58) Field of Search .................. 435/320.1, 325, 435/7.1, 366, 8; 530/399; 536/24.1

(56) References Cited

U.S. PATENT DOCUMENTS

| | | |
|---|---|---|
| 4,508,828 A | 4/1985 | Lindall et al. |
| 5,298,429 A | 3/1994 | Evans et al. |
| 5,494,806 A | 2/1996 | Segre et al. |

OTHER PUBLICATIONS

Huang, et al, 1996, J. Biol. Chem.52: 33382.*
Yu, et al, 1997, Endocrinol., 138: 3085.*
Zhengmin, H. et al. 1996, J. Biol. Chem. 271(52):33382–33389, esp. Fig. 2.*
Yu, X, et al. 1997, Endocrinol. 138(8): 3085–3092, esp. p. 3087 and 3090.*
Babichuk et al., In Vivo Regulation of Murine Granzyme B Gene Transcription in Activated Primary T Cells, The Journal of Biological Chemistry 271(28), 16485–16493 (1996).
Migeon et al., Regulation of cAMP–mediated Gene Transcription by Wild Type a Mutated G–protein alpha Subunits, The Journal of Biological Chemistry 269(46), 29146–29152 (1994).
Gao et al., Functional Importance of the Cyclic AMP Response Element–Like Decamer Motif in the CD8alpha Promoter, The Journal of Immunology 150(10), 4376–4385 (1993).
Himmler et al., Functional Testing of Human Dopamine D1 and D5 Receptors Expressed In Stable cAMP–Responsive Luciferase Reporter Cell Lines, Journal of Receptor Research 13(1–4), 79–94 (1993).
Castanon et al., Functional Coupling Of Human Adenosine Receptors To A Ligand–Dependent Reporter Gene System, Biochemical & Biophysical Research Communications 198(2), 626–631 (1994).
Reeck et al., "Homology" in Proteins and Nucleic Acids: A Terminology Muddle and a Way out of It, Cell, 50, 667 (1987).
Germain et al., Transcription induction of the human renin gene by cyclic AMP requires cyclic AMP response element––binding protein (CREB) and a factor binding a pituitary–specific trans–acting factor (Pit–1) motif, Journal of Biochem 316, 107–113 (1996).
Ghozi et al., Expression of the human acute myeloid leukemia gene AML1 is regulated by two promoter regions, Proc. Natl. Acad. Sci. 93, 1935–1940 (1996).
Tilly et al., Expression of Recombinant Human Follicle–Stimulating Hormone Receptor: Species–Specific Ligand Binding, Signal Transduction, and Identification of Multiple Ovarian Messenger Ribonucleic Acid Transcripts, Endocrinology 131(2) 799–806 (1992).
Taylor et al., The use of phosphorothioate–modified DNA in restriction enzyme reactions to prepare nicked DNA, Nucleic Acids Research 13(24, 8749–8764 (1985).
Pei et al., Regulation of the alpha Inhibin Gene by Cyclic Adenosine 3',5'–Monophosphate after Transfection into Rat Granulosa Cells, Molecular Endocrinology 5(4), 521–534 (1991).
Stachowiak et al., Regulation of tyrosine hydorxylase gene expression in depolarized non–transformed bovine adrenal medullary cells: second messenger systems and promoter mechanisms, Molecular Brain Research 22, 309–319 (1994).
Saiki et al., Enzymatic Amplification of Beta–Globin Genomic Sequences and Restriction Site Analysis for Diagnosis of Sickle Cell Anemia, Science 230, 1350–1354 (1985).
Sanger et al., DNA Sequencing with Chain–Terminating Inhibitors, Prco. Natl. Acad. Sci. 74(12) 5463–5467 (1977).
Spengler et al., Differential signal transduction by five splice variants of the PACAP receptor, Nature 365, 170–175 (1993).
Mullis et al., Specific Synthesis of DNA in Vitro via a Polymerase–Catalyzed Chain Reaction, Methods in Enzymology 155, 335–350 (1987).
Pines et al., Generation and Characterization of Human Kidney Cell Lines Stably Expressing Recombinant Human PTH/PTHrP Receptor: Lack of Interaction With A C–Terminal Human PTH Peptide, Endocrimology 135(4), 1713–1716 (1994).
Fluehmann B. et al., Parathyroid Hormone Responses of Cyclic AMP–, Serum–and Phorbol Ester–responsive Reporter Genes in Osteoblast–like UMR–106 Cells, Molecular and Cellular Endocrinology 139 (1998) 89–98.

* cited by examiner

*Primary Examiner*—Elizabeth Kemmerer
*Assistant Examiner*—Sandra Wegert
(74) *Attorney, Agent, or Firm*—F. Aaron Dubberley

(57) ABSTRACT

This invention is directed to a bioassay for determining the functionality of parathyroid hormone compounds. More particularly, this invention is directed to a bioassay wherein the compound to be tested is added to a culture of parathyroid hormone receptor expressing cells bearing a reporter gene under the transcriptional control of multiple c-AMP responsive elements.

7 Claims, 1 Drawing Sheet

LUCIFERASE REPORTER BIOASSAY OF PARATHYROID HORMONE COMPOUNDS

This application claims the benefit of copending provisional application, No. 60/099,188, which was filed Sep. 4, 1998.

FIELD OF THE INVENTION

This invention is directed to a bioassay for determining the functionality of parathyroid hormone compounds. More particularly, this invention is directed to a bioassay wherein the compound to be tested is added to a culture of parathyroid hormone receptor expressing cells bearing a reporter gene under the transcriptional control of multiple c-AMP responsive elements. Still more particularly, this invention is directed to a bioassay wherein the compound to be tested is added to a culture of parathyroid hormone receptor expressing cells bearing a luciferase reporter gene under the transcriptional control of multiple c-AMP responsive elements.

BACKGROUND OF THE INVENTION

Human parathyroid hormone (hPTH) is an 84 amino acid protein which is a major regulator of calcium homeostasis. Parathyroid hormone-related protein (hPTHrP) is a 139 to 171 amino acid protein with N-terminal homology to hPTH. The N-terminal fragments of hPTH and hPTHrP, particularly those consisting of amino acids 1–34, retain the full biological activity of the parent hormone.

The biological activity of hPTH is reflected in the activation of two secondary messenger systems: G-protein coupled adenylyl cyclase (AC) and protein kinase C (PKC) activity. The N-terminal fragments hPTH(1–34)OH and hPTH(1–31)NH$_2$ have been demonstrated to be anabolic with respect to bone formation in humans and ovariectomized rats, respectively. This increase in bone growth has been demonstrated to be coupled with stimulation of adenylyl cyclase activity. Analogs of these N-terminal fragments have significant therapeutic potential for the treatment of physiological conditions associated with bone cell calcium regulation including hypocalcemia; osteoporosis; osteopenia; and disorders associated with osteoporosis and osteopenia such as hyperparathyroidism, hypoparathyroidism, and Cushings syndrome; glucocorticoid- and immunosuppressant-induced osteopaenia; and bone fracture and bone refracture repair.

To facilitate the discovery of efficacious hPTH analogs, a need exists for methods of determining the functionality of these analogs. Such a method should be simple, sensitive, and lend itself to automation so that a multiplicity of compounds can be rapidly screened.

SUMMARY OF THE INVENTION

This invention is directed to a bioassay for determining the functionality of a parathyroid hormone compound comprising
  (a) adding the compound to a culture of parathyroid hormone receptor expressing cells bearing a reporter gene under the transcriptional control of multiple cAMP responsive elements; and
  (b) measuring the change in expression of the reporter gene. Preferably, the change in reporter gene expression is compared to appropriate control levels of reporter gene expression. Appropriate controls which may be measured include, but are not limited to, expression in the absence of the parathyroid hormone compound and/or expression in the presence of a known parathyroid hormone receptor agonist. Parathyroid hormone receptor agonists include, but are not limited to, hPTH(1–34)OH and hPTH(1–31)NH$_2$.

The cells may be prokaryotic or eukaryotic cells. Preferably, the cells are mammalian cells. The cells may comprise an endogenous or heterologous nucleic acid encoding the parathyroid hormone receptor. Preferably, the cells comprise a heterologous nucleic acid encoding the parathyroid hormone receptor.

The number of cAMP responsive elements should be sufficient to drive expression within the cell of the reporter gene in the presence of cAMP. Preferably, the number of cAMP responsive elements is greater than about 10. More preferably, the number of cAMP responsive elements is about 16.

The reporter gene may encode a protein selected from, but not limited to, β-galactosidase, chloramphenicol acetyltransferase, β-glucuronidase, and luciferase. A preferred reporter gene encodes luciferase.

DETAILED DESCRIPTION OF THE INVENTION

Figure 1:
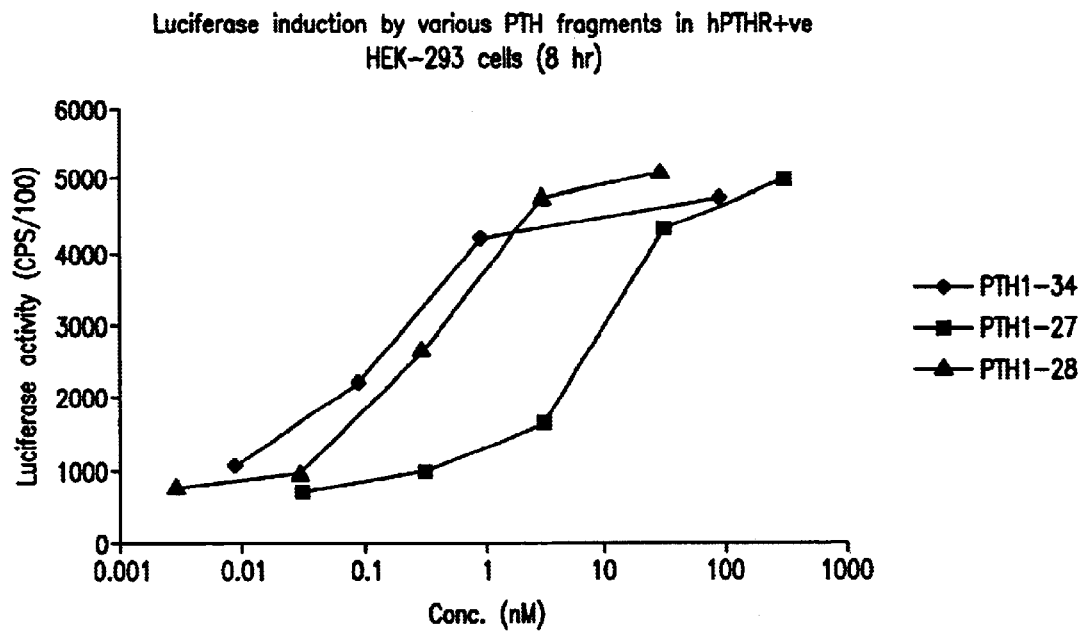
FIG. 1 is a plot of luciferase induction in hPTH receptor-expressing HEK-293 cells bearing the luciferase reporter gene, following induction for 8 hours with hPTH(1–34), represented by the filled-in diamonds, hPTH(1–27), represented by the filled in squares, and hPTH(1–28), represented by the filled in triangles.

The various aspects of the invention will be set forth in greater detail in the following sections. This organization into various sections is intended to facilitate understanding of the invention, and is in no way intended to be limiting thereof.

Definitions

The following defined terms are used throughout the present specification, and should be helpful in understanding the scope and practice of the present invention.

In a specific embodiment, the term "about" or "approximately" means within 20%, preferably within 10%, and more preferably within 5% of a given value or range.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

A "gene" refers to an assembly of nucleotides that encode a polypeptide, and includes cDNA and genomic DNA nucleic acids.

A "recombinant DNA molecule" is a DNA molecule that has undergone a molecular biological manipulation.

A "vector" is any means for the transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. Viral vectors include retrovirus, adeno-associated virus, pox, baculovirus, vaccinia, herpes simplex, Epstein-Barr and adenovirus vectors, as set forth in greater detail below. Non-viral vectors include plasmids, liposomes, electrically charged lipids (cytofectins), DNA-protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

A "cloning vector" is a replicon, such as plasmid, phage or cosmid, to which another DNA segment may be attached so as to bring about the replication of the attached segment. Cloning vectors may be capable of replication in one cell type, and expression in another ("shuttle vector").

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. The transforming DNA can be integrated (covalently linked) into chromosomal DNA making up the genome of the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook, Fritsch & Maniatis, *Molecular Cloning: A Laboratory Manual*, Second Edition (1989) Cold Spring Harbor Laboratory Press, Cold Spring Harbor, N.Y., 11.7–11.8). Preferably a minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis T. et al., "Molecular Cloning, a Laboratory Manual", Cold Spring Harbor Laboratory, Cold Spring Harbor, N.Y., 1982; ($2^{nd}$ Ed. 1989).

A "signal sequence" may be included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin which are responsible for expressing different proteins or even synthetic proteins (a heterologous region). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, promoters, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"Heterologous" DNA refers to DNA not naturally located in the cell, or in a chromosomal site of the cell. Preferably, the heterologous DNA includes a gene foreign to the cell.

A "polypeptide" is a polymeric compound comprised of covalently linked amino acid residues. Amino acids have the following general structure:

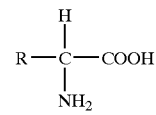

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide which plays a structural or functional role in a living cell.

The terms "parathyroid hormone" and "PTH" mean human parathyroid hormone (hPTH) and human parathyroid hormone related protein (hPTHrP).

A "variant" of a PTH or hPTHrP polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art.

If such allelic variations, analogues, fragments, derivatives, mutants, and modifications, including alternative mRNA splicing forms and alternative post-translational modification forms result in derivatives of the polypeptide which retain any of the biological properties of the polypeptide, they are intended to be included within the scope of this invention.

A "heterologous protein" refers to a protein not naturally produced in the cell.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

The term "parathyroid hormone compound" means parathyroid hormone as defined herein or fragments, variants or analogs thereof. The term "analog" means any compound capable of binding to a parathyroid receptor. Parathyroid hormone compounds may be derivatives of the parent human parathyroid hormone or human parathyroid hormone related protein. Such derivatives are denoted using numbers in parenthesis to refer to the number of amino acid residues in the peptide compound, beginning at the N-terminus. For Example, hPTH(1–34) is a parathyroid hormone compound comprising the first 34 amino acids of human parathyroid hormone.

The terms "parathyroid receptor" and "PTH receptor" mean the naturally occurring or "wild type" or cognate human parathyroid hormone receptor or operational modified or genetically engineered homologs of the corresponding naturally occurring cognate receptor. The term "operational" when used in connection with modified or genetically engineered homologs of parathyroid receptor means that the modified or genetically engineered receptor works for its intended purpose.

"Functionality" of a parathyroid hormone compound relates to its ability to bind parathyroid hormone receptor and stimulate or inhibit production of intracellular cAMP. Preferably, the functionality is stimulation of cAMP production.

The term "reporter gene" means a coding sequence attached to heterologous promoter or enhancer elements, and whose product is easily and quantifiably assayed when the construct is introduced into cells. According to the present invention, the heterologous promoter comprises multiple cAMP responsive elements, which upon binding of cAMP, drives the expression of the gene. The introduction of reporter genes into cells is described in U.S. Pat. No. : 5,298,429, incorporated herein by reference. Representative reporter genes include bacterial genes encoding β-galactosidase (lacZ), chloramphenicol acetyltransferase (cat), β-glucuronidase (GUS), and the like, and luciferase. A preferred reporter gene is luciferase. The use of luciferase as a reporter gene is described in the following publications, incorporated herein by reference.

1. Babichuk, et. al., 1996, *Journal of Biological Chemistry*, 1996, 271 (28), 16485–16493.
2. Castanon, et. al., *Biochemical and Biophysical Research Communications*, 1994, 198 (2), 626–631.
3. Gao, et. al., *Journal of Immunology*, 1993, 150 (10), 4376–4385;
4. Germain, et. al., *Biochemical Journal*, 1996, 316, 107–113;
5. Ghozi, et. al., *Proc. Natl. Acad. Sci. USA*, 1996, 93, 1935–1940;
6. Himmler, et. al., *Journal of Receptor Research*, 1993, 13 (1–4), 79–94;
7. Midgeon, et. al., *Journal of Biological Chemistry*, 1994, 269 (46), 29146–29152.
8. Pei, et. al., *Molecular Endocrinology*, 1991, 5 (4), 521–534;
9. Stachowiak, et. al., *Brain Research. Molecular Brain Research*, 1994, 22 (1–4), 309–319; and
10. Tilly, et. al., *Encocrinology*, 1992, 131 (2), 799–806.

The bioassay of the present invention is constructed by introducing a reporter gene into cells expressing a PTH receptor. The reporter gene contains in its promoter region multiple cAMP responsive elements which upon binding of cAMP drives the expression of the gene. Thus, the extent of reporter gene expression will vary as a function of cAMP level in the cell. Upon binding a parathyroid hormone compound, the PTH receptor stimulates the production of intracellular cAMP, the extent of which is dependent on the magnitude of receptor activation by the parathyroid hormone compound. The receptor-mediated increase in cAMP is therefore coupled to the increase in expression of the reporter gene. By measuring the expression of the reporter gene, the activation of the PTH receptor by parathyroid hormone compounds can be readily measured.

One skilled in the art will readily appreciate that the present invention is well adapted to carry out the objects of the invention and obtain the ends and advantages mentioned, as well as those inherent therein. The examples described below are presented as representative of the preferred embodiments, or intended to be exemplary and not intended as limitations on the scope of the present invention.

EXAMPLES

General molecular biology techniques

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, protein extraction with phenol or phenol/chloroform, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; ($2^{nd}$ Ed. 1989); Ausubel F. M. et al. (eds), "Current Protocols in Molecular Biology", John Wiley & Sons, New York, 1987].

Conventional cloning vehicles include pBR322 and pUC type plasmids and phages of the M13 series. These may be obtained commercially (Bethesda Research Laboratories).

For ligation, DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling in of 5' protruding ends may be performed with the Kienow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides may be performed according to the method developed by Taylor et al. [Nucleic Acids Res. 13 (1985) 8749–8764] using the kit distributed by Amersham.

The enzymatic amplification of DNA fragments by PCR [Polymerase-catalyzed Chain Reaction, Saiki R. K. et al., Science 230 (1985) 1350–1354; Mullis K. B. and Faloona F.

A., Meth. Enzym. 155 (1987) 335–350] technique may be performed using a "DNA thermal cycler" (Perkin Elmer) according to the manufacturer's specifications.

Verification of nucleotide sequences may be performed by the method developed by Sanger et al. [Proc. Natl. Acad. Sci. USA, 74 (1977) 5463–5467] using the kit distributed by Amersham.

Plasmid DNAs may be purified by the Qiagen Plasmid Purification System according to the manufacture's instruction.

Human PTH Receptor-Expressing HEK-293 Cells

This cell line is obtained as described by Pines et al., Endocrinology, 1994, 135(4), 1713–1716, incorporated herein by reference.

Luciferase Reporter Gene

The firefly luciferase reporter gene bearing the cAMP responsive elements is amplified by PCR from the pDMC16LUC vector using the method of Spengler et al., Nature, 1993, 365: 170–175, incorporated herein by reference. The PCR product containing the MMTV promoter, sixteen cAMP responsive elements and the luciferase gene is inserted into the zeocin resistant vector (pUTSV1 from InVitrogen). The final vector, termed pMCL3zeo, is then introduced into PTH receptor expressing HEK-293 cells using the lipofectamine method (reagents and method obtained from Gibco/BRL). Cells incorporating the luciferase reporter gene are selected by including zeocin in the culture medium. By limited dilution, different cell clones are isolated and expanded. These clones are tested for their responsiveness to PTH in terms of luciferase expression. Clones that exhibited 5–6 fold luciferase induction by PTH are used for assay development.

Luciferase Reporter Assay Procedure hPTH receptor-expressing HEK-293 cells bearing the luciferase reporter gene are cultured to 80–90% confluency. To assess the ability of an agent to interact with the PTH receptor, the test compound is added to the culture media at the appropriate dilution. hPTH(1–34) is used as the positive control. Induction of luciferase expression is conducted at 37° C. Following induction, the culture medium is removed and the cell is lysed by adding the lysis buffer (Luciferase assay kit from Promega Corp.). The lysates are aliquoted to a black 96 well plate. The luciferase activity in the lysates is measured by the addition of the luciferin substrate (Promega assay kit) to effect light production. The output of light is measured in a Wallac Trilux microbeta plate reader.

The luciferase activity of hPTH receptor-expressing HEK-293 cells bearing the luciferase reporter gene following induction for 8 hours with hPTH(1–34), hPTH(1–27) and hPTH(1–28) is shown in FIG. 1.

Figure 2:
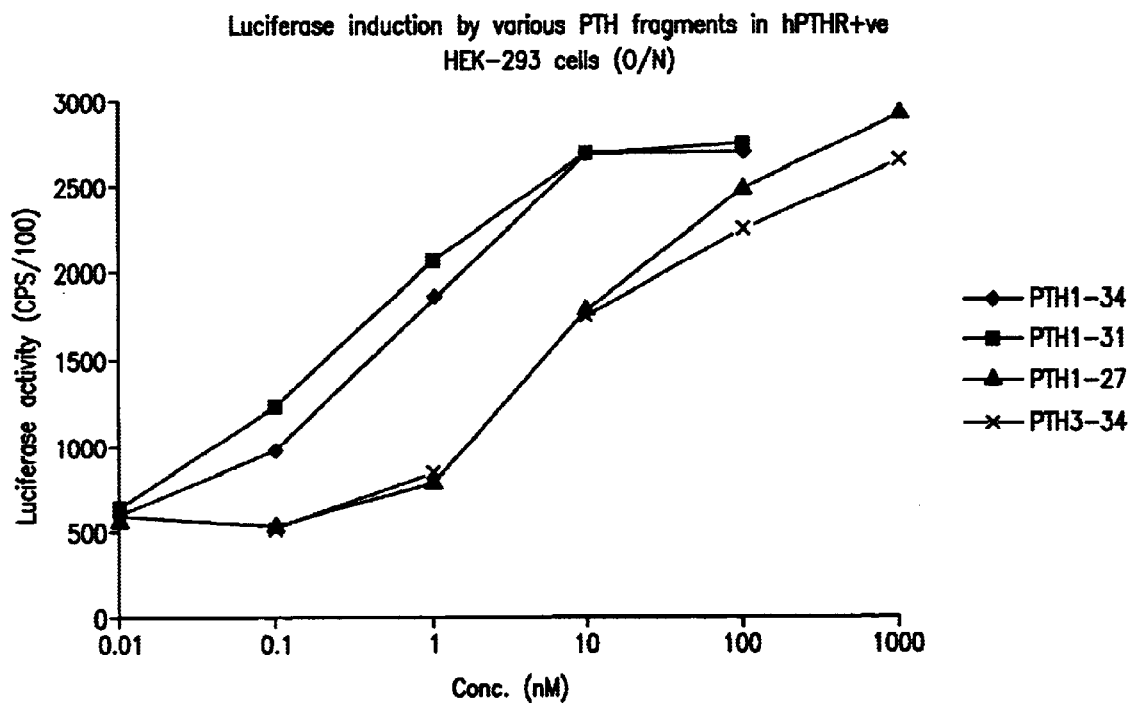
FIG. 2 is a plot of luciferase induction in hPTH receptor-expressing HEK-293 cells bearing the luciferase reporter gene, following induction overnight (about 16 hours) with hPTH(1–34), represented by the filled-in diamonds, hPTH (1–31), represented by the filled in squares, hPTH(1–27), represented by the filled in triangles and hPTH(3–34), represented by the symbol "X".

The luciferase activity of hPTH receptor-expressing HEK-293 cells bearing the luciferase reporter gene following induction overnight (about 16 hours) with hPTH(1–34), hPTH(1–31), hPTH(1–27) and hPTH(3–34) is shown in FIG. 2.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method for determining the functionality of a parathyroid hormone compound, the method comprising
   (a) adding the compound to a culture of parathyroid hormone receptor expressing cells bearing a reporter gene under the transcriptional control of multiple cAMP responsive elements, and then measuring the expression of the reporter gene; and
   (b) comparing the measured expression of step (a) with the measured expression of the reporter gene in a control culture comprising:
      (i) the parathyroid hormone receptor expressing cells bearing the reporter gene under the transcriptional control of multiple cAMP response elements, and a parathyroid hormone, a parathyroid hormone-related protein, a parathyroid receptor agonist, or a combination thereof, or
      (ii) the parathyroid hormone receptor expressing cells bearing a reporter gene under the transcriptional control of multiple cAMP responsive elements, in the absence of the parathyroid hormone compound, wherein a difference between the measured expression of step (a) and the measured expression of the control culture is indicative of the functionality of the parathyroid hormone compound, and wherein the number of cAMP responsive elements is greater than about 10.

2. The method according to claim 1, wherein the number of cAMP responsive elements is about 16.

3. The method according to claim 2, wherein the cells are mammalian cells.

4. The method according to claim 2, wherein the cells comprise a heterologous nucleic acid encoding the parathyroid hormone receptor.

5. The method according to claim 2, wherein the reporter gene encodes a protein selected from the group consisting of β-galactosidase, chloramphenicol acetyltransferase, β-glucuronidase, and luciferase.

6. The method according to claim 5, wherein the reporter gene encodes luciferase.

7. The method according to claim 2, wherein the parathyroid hormone receptor is human parathyroid hormone receptor.

* * * * *